(12) United States Patent
Matsushita et al.

(10) Patent No.: US 7,529,631 B2
(45) Date of Patent: May 5, 2009

(54) DEFECT DETECTION SYSTEM, DEFECT DETECTION METHOD, AND DEFECT DETECTION PROGRAM

(75) Inventors: Hiroshi Matsushita, Hiratsuka (JP); Yasutaka Arakawa, Yokohama (JP); Junji Sugamoto, Oita (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/812,398

(22) Filed: Jun. 19, 2007

(65) Prior Publication Data

US 2008/0004823 A1  Jan. 3, 2008

(30) Foreign Application Priority Data

Jun. 20, 2006  (JP)  .............................. 2006-170677

(51) Int. Cl.
*G01B 5/30* (2006.01)
(52) U.S. Cl. ......................................... 702/35; 702/82
(58) Field of Classification Search .................. 702/34, 702/35, 81, 82, 84
See application file for complete search history.

(56) References Cited

U.S. PATENT DOCUMENTS 7,138,283 B2   11/2006  Matsushita et al.
7,221,991 B2   5/2007   Matsushita et al.
7,222,026 B2   5/2007   Matsushita et al.
2004/0255198 A1  12/2004  Matsushita et al.
2005/0097481 A1*  5/2005  Mitsutake et al. .............. 716/2

FOREIGN PATENT DOCUMENTS

JP  2002-359266  12/2002

* cited by examiner

*Primary Examiner*—Michael P Nghiem
(74) *Attorney, Agent, or Firm*—Finnegan, Henderson, Farabow, Garrett & Dunner, L.L.P.

(57) ABSTRACT

A defect detection system includes a data acquiring section that acquires time series data of device parameter of each manufacturing device including an exposure device, and information on defect distribution in an area with a size smaller than a chip area size, a pattern classifying section that assembles the information on the defect distribution in units of shot or chip areas, and classifies the distributions to a defect pattern, a feature quantity calculating section that processes the time series data and calculates a feature quantity, a significant difference test section that calculates occurrence frequency distributions of the shot or chip area wherein the defect pattern to the feature quantity exists and does not exist, respectively, and determines the presence/absence of significant difference between the frequency distributions, and a defect detecting section that detects the device parameter corresponding to the feature quantity as the cause of defect of the defect pattern.

19 Claims, 14 Drawing Sheets

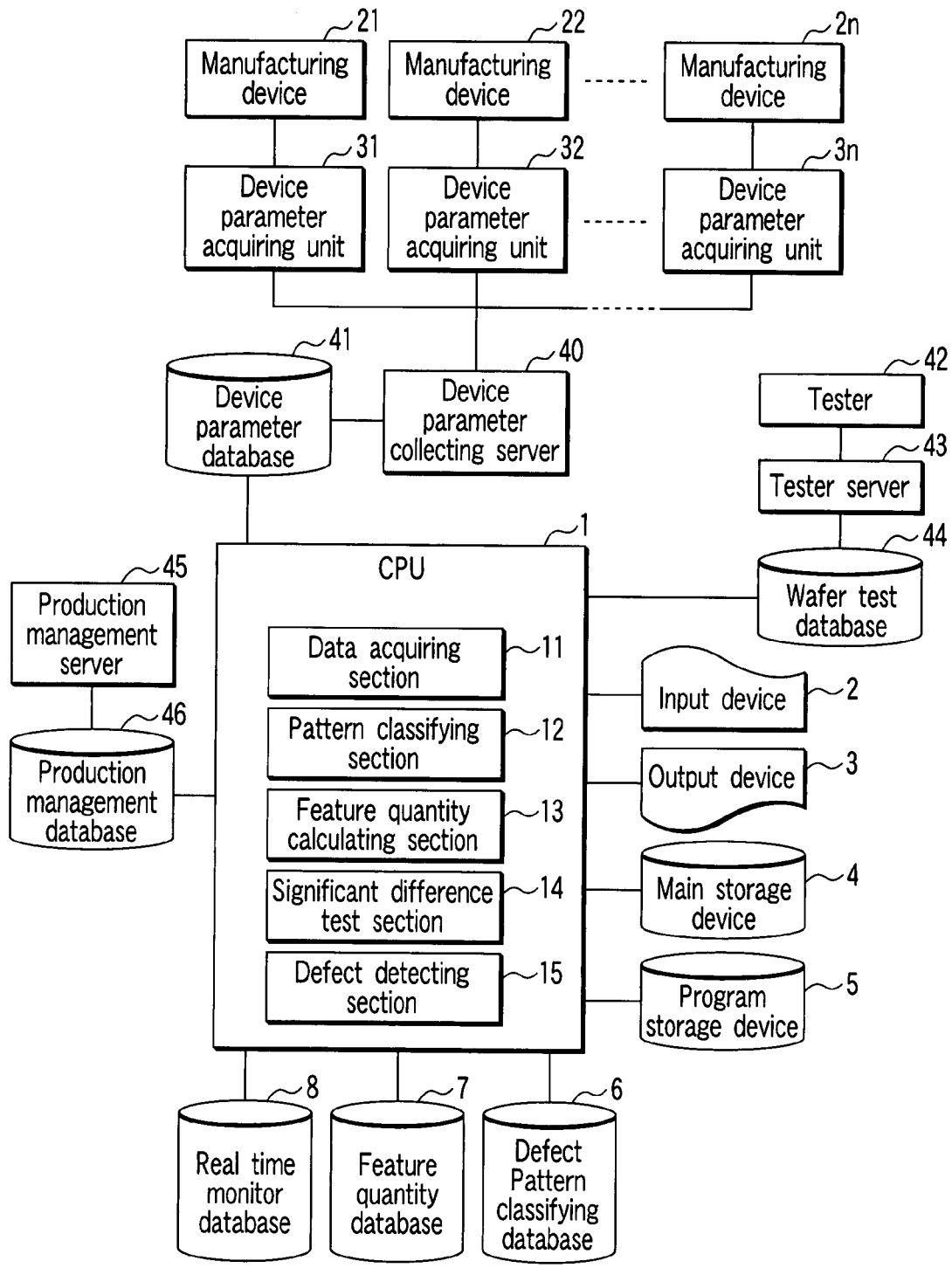
F I G. 1

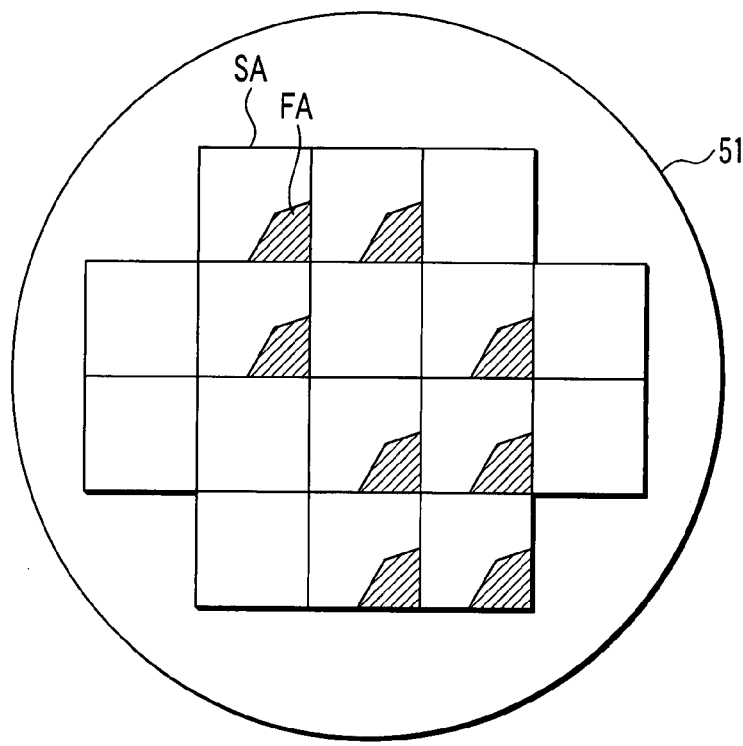
F I G. 4
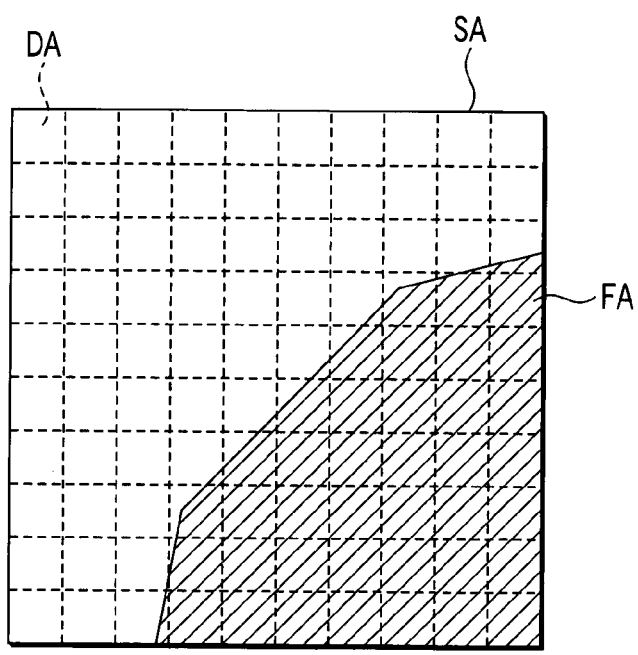
F I G. 5

FIG. 12

| Product name | Lot number | Wafer number | Chip number | Shot number | Defect pattern classification number | Device parameter waveform feature quantity number [1] | Device parameter waveform feature quantity number [2] | |
|---|---|---|---|---|---|---|---|---|
| A | #10 | #8 | #10 | #10 | [2] | 0.36 | 0.63 | |
| A | #50 | #10 | #15 | #15 | [1] | 0.92 | 0.72 | |
| A | #45 | #20 | #3 | #3 | [3] | 0.11 | 0.12 | |

FIG. 13

| Device parameter waveform feature quantity number [i] | Defect pattern classification number [1] | | Significant difference test value Pij |
|---|---|---|---|
| | Abnormal shot | Normal shot | |
| [1] | Frequency (a.u.) vs Device parameter waveform feature quantity value | Frequency (a.u.) vs Device parameter waveform feature quantity value | $P_{11} > 0.05$ |

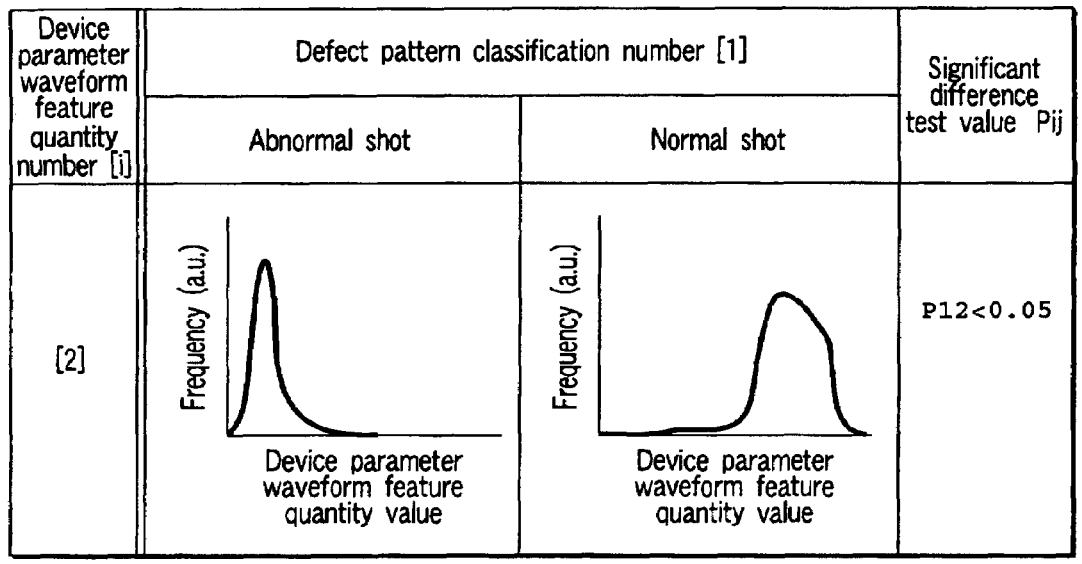

FIG. 14

| Defect pattern classification number | Device parameter waveform feature quantity number | | | | | |
|---|---|---|---|---|---|---|
| | [1] Exposure amount | [2] Synchronization precision | [3] Humidity in unit | [4] Focus following | [5] Rotation correction amount | [6] Developing solution temperature |
| [1] | Significant | | | | | |
| [2] | | | Significant | | | |
| [3] | | Significant | | | | |

FIG. 15

| Defect pattern classification number | Process | Manufacturing device | Device parameter | Feature quantity algorithm |
|---|---|---|---|---|
| [1] | Lithography | X | Exposure amount | Maximum value |
| [2] | Lithography | Y | Humidity in unit | Maximum value |
| [3] | Lithography | Z | Synchronization precision | Maximum value |

FIG. 16

| | Normal ↓ First machine | Second machine | Abnormal ↓ Third machine | Fourth machine | |
|---|---|---|---|---|---|
| Step A | □ | □ | ▨ | | Pattern 1 |
| Step B | ▨ | □ | □ | □ | Pattern 2 |
| Step C | □ | □ | | | |
| Step D | □ | ▨ | □ | | Pattern 3 |

DEFECT DETECTION SYSTEM, DEFECT DETECTION METHOD, AND DEFECT DETECTION PROGRAM

CROSS-REFERENCE TO RELATED APPLICATIONS

This application is based upon and claims the benefit of priority from prior Japanese Patent Application No. 2006-170677, filed Jun. 20, 2006, the entire contents of which are incorporated herein by reference.

BACKGROUND OF THE INVENTION

1. Field of the Invention

The present invention relates to manufacturing of a semiconductor device, in particular, to a defect detection system, a defect detection method, and a defect detection program for detecting the cause of a defect of the semiconductor device.

2. Description of the Related Art

One of the problems to be addressed in enhancing the productivity of the semiconductor device such as a large-scale integration (LSI) circuit is to enhance the yield. It is important to analyze the yield loss, and ascertain and improve the process, manufacturing device, or design conditions that lead to the cause of yield loss at an early stage in order to enhance the yield. However, for example, the LSI is produced through hundreds of steps and manufacturing devices. Thus, it is generally very difficult to detect that the cause of a defect that occurred in the LSI once.

The result of the wafer test, which is the electrical characteristic test, performed after the termination of the wafer process of the semiconductor device manufacturing provides an important clue in ascertaining the cause of the defect. This is because the wafer test is performed on the wafer in a wafer shaped state. That is, the position of the defective portion in the wafer surface is detected in the wafer test by mapping displaying the wafer test result in the wafer surface. A typical mapping display is a failure bit map (FBM) acquired in memory products. In logic products, memory mixed logic products, or the like, a pass/fail map in which the non-defective product (pass) or defective product (fail) is mapping displayed in units of chip partitions.

The distribution of the defect in the wafer surface is broadly divided into two types of a "random defect" that occurs equally in the wafer surface and a "clustering defect" that occurs deflected to one part. Most of the time, the occurrence of the clustering defect arises from systematic causes resulting from process, manufacturing device and the like, which is a great cause in lowering of yield. The defect resulting from process, manufacturing device and the like produces a defect pattern inherent in the process or the manufacturing device on the wafer surface. Therefore, pattern analysis of the clustering defect is considered as the clue to ascertain the cause of occurrence of defects.

The defect detection in the semiconductor device manufacturing is performed by researching the manufacturing history in a clean room for a plurality of wafers or a plurality of lots in which the same clustering defect has occurred. For example, a method of researching whether or not the same step is processed by the same manufacturing device for the plurality of wafers in which the same clustering defect has occurred, and performing a significant difference test between the manufacturing devices for the feature quantity obtained by quantifying the clustering defect (see, e.g., Jpn. Pat. Appln. KOKAI Publication No. 2002-359266).

However, the clustering defect in manufacturing of the semiconductor device does not only appear as a pattern in the wafer surface. For example, the clustering defect resulting from the lithography step appears as a pattern in the processing unit of the lithography step, that is, the shot area. The state of the processing process differs between the central part and the peripheral part of the memory cell array in memory products, and thus defects occur in the state deflected towards the peripheral part of the memory cell array, in which case, the pattern of the clustering defect is produced in the chip partition.

Conventionally, pattern classification of the clustering defect and defect detection are performed using the wafer test result indicating the defects in units of partition with a size larger than or equal to a size of the chip partition. However, when the wafer test result indicating the defects in units of partition with a size larger than or equal to the size of the chip partition is used, pattern classification of the clustering defect and defect detection in the shot partition or the chip partition cannot be performed, and the cause of defect of the semiconductor device cannot be detected at high precision.

BRIEF SUMMARY OF THE INVENTION

According to an aspect of the present invention, a defect detection system is provided, the defect detection system including:

a data acquiring section that acquires time series data of device parameter of each of a plurality of manufacturing devices including an exposure device, and information on defect distribution in an area with a size smaller than a size of each of a plurality of chip areas arranged on a wafer processed in each of the plurality of manufacturing devices;

a pattern classifying section that assembles the information on the defect distribution in units of shot areas of the exposure device or in units of chip areas, and classifies the assembled defect distributions to a defect pattern;

a feature quantity calculating section that statistically processes the time series data and calculates a feature quantity;

a significant difference test section that calculates an occurrence frequency distribution of the shot area or the chip area in which the defect pattern with respect to the feature quantity exists and an occurrence frequency distribution of the shot area or the chip area in which the defect pattern with respect to the feature quantity does not exist, and determines the presence or absence of significant difference between the frequency distributions; and a defect detecting section that detects the device parameter corresponding to the feature quantity as the cause of defect of the defect pattern when it is determined that the significant difference exists.

According to another aspect of the present invention, a defect detection method is provided, the method including the steps of:

acquiring time series data of device parameter of each of a plurality of manufacturing devices including an exposure device;

acquiring information on defect distribution in an area with a size smaller than a size of each of a plurality of chip areas arranged on a wafer processed in each of the plurality of manufacturing devices;

assembling the information on the defect distribution in units of shot areas of the exposure device or in units of chip areas, and classifying the assembled defect distributions to a defect pattern;

statistically processing the time series data and calculating a feature quantity;

calculating an occurrence frequency distribution of the shot area or the chip area in which the defect pattern with respect to the feature quantity exists and an occurrence frequency distribution of the shot area or the chip area in which the defect pattern with respect to the feature quantity does not exist;

determining the presence or absence of significant difference between the frequency distributions; and detecting the device parameter corresponding to the feature quantity as the cause of defect of the defect pattern when it is determined that the significant difference exists.

According to a further aspect of the present invention, program for a computer to execute commands is provided, the program including the commands of:

acquiring time series data of device parameter of each of a plurality of manufacturing devices including an exposure device;

acquiring information on defect distribution in an area with a size smaller than a size of each of a plurality of chip areas arranged on a wafer processed in each of the plurality of manufacturing devices;

assembling the information on the defect distribution in units of shot areas of the exposure device or in units of chip areas, and classifying the assembled defect distributions to a defect pattern;

statistically processing the time series data and calculating a feature quantity;

calculating an occurrence frequency distribution of the shot area or the chip area in which the defect pattern with respect to the feature quantity exists and an occurrence frequency distribution of the shot area or the chip area in which the defect pattern with respect to the feature quantity does not exist;

determining the presence or absence of significant difference between the frequency distributions; and detecting the device parameter corresponding to the feature quantity as the cause of defect of the defect pattern when it is determined that the significant difference exists.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing one example of a configuration of a defect detection system according to an embodiment of the present invention;

FIG. 4 is a schematic view showing one example of sub-chip test data according to the embodiment of the present invention;

FIG. 5 is a schematic view showing one example of a defect distribution in a shot partition according to the embodiment of the present invention;

FIG. 12 is a table showing one example of an association of the device parameter waveform feature quantity (i.e., feature quantified time series data of device parameter) and the defect pattern according to the embodiment of the present invention;

FIG. 13 is a table for describing a significant difference test according to the embodiment of the present invention;

FIG. 14 is another table for explaining a significant difference test according to the embodiment of the present invention;

FIG. 15 is a table showing one example of a significant difference test result according to the embodiment of the present invention;

FIG. 16 is a table showing one example of a defect detection result according to the embodiment of the present invention;

DETAILED DESCRIPTION OF THE INVENTION

Figure 2:
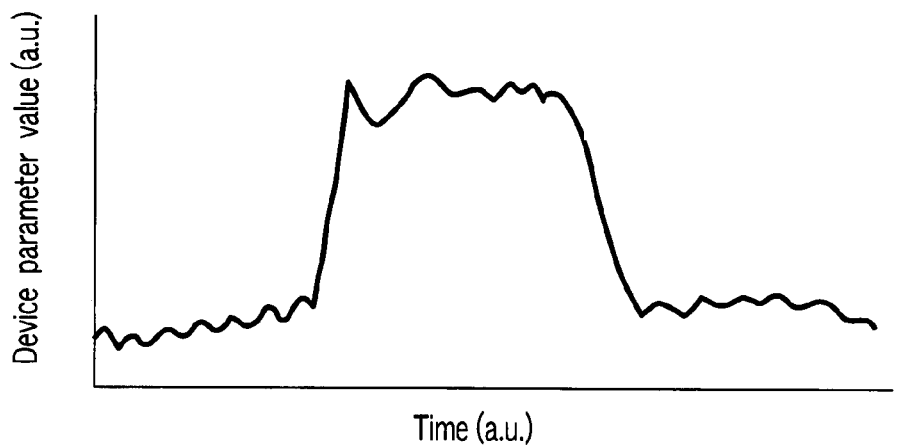
FIG. 2 is a graph showing one example of time series data of device parameters according to the embodiment of the present invention.

The embodiments of the present invention will now be described with reference to the following drawings. Same or similar reference characters are denoted for same or similar components throughout the description of the drawings.

A defect detection system according to the present embodiment includes a central processing unit (CPU) 1, a device parameter database 41, a production management database 46, a wafer test database 44, a defect pattern classification database 6, a feature quantity database 7, and a real time monitor database 8, which are connected to the CPU 1, as shown in FIG. 1.

The CPU 1 includes a data acquiring section 11 that acquires the time series data of device parameters for each of a plurality of manufacturing devices 21, 22, . . . , 2n including an exposure device and information on defect distribution in an area with a size smaller than the size of each of a plurality of chip areas arrayed on the wafer to be processed in each of the plurality of manufacturing devices 21, 22, . . . , 2n; a pattern classifying section 12 that assembles the information on the defect distribution in unit of shot areas of the exposure device or in unit of chip areas, and classifies the assembled defect distribution to a defect pattern; a feature quantity calculating section 13 that statistically processes the time series data and calculates the feature quantity; a significant difference test section 14 that calculates an occurrence frequency distribution of a shot area or a chip area in which the defect pattern with respect to the feature quantity exists and an occurrence frequency distribution of a shot area or a chip area in which the defect pattern with respect to the feature quantity does not exist, and determines the presence or absence of significant difference between the frequency distributions; and a defect detecting section 15 that detects the device parameter corresponding to the feature quantity as the cause of defect of the defect pattern when it is determined that the significant difference exists. Details of the data acquiring section 11, the pattern classifying section 12, the feature quantity calculating section 13, the significant difference test section 14, and the defect detecting section 15 of the CPU 1 will be hereinafter described.

The device parameter database 41 is connected to a device parameter collecting server 40. The device parameter collecting server 40 is connected to a device parameter acquiring units 31, 32, . . . , 3n. The device parameter acquiring units 31, 32, . . . , 3n are respectively connected to the manufacturing devices 21, 22, . . . , 2n.

The manufacturing devices 21, 22, . . . , 2n include various semiconductor manufacturing devices such as ion injection device, impurity dispersion device, thermal oxidation device, chemical vapor deposition (CVD) device, heat processing device, sputtering device, vacuum deposition device, plating process device, chemical mechanical polishing (CMP) device, dry or wet etching device, washing device, exposure device, dicing device, bonding device and the like. The manufacturing devices 21, 22, . . . , 2n may also include auxiliary equipments such as pure water manufacturing device and gas purifying device. In addition, these manufacturing devices 21, 22, . . . , 2n are applicable to either a batch type device or a sheet type device.

A plurality of device parameters indicating the operation state of the manufacturing devices 21, 22, . . . , 2n, operating condition setting value, and the like is output from each manufacturing device 21, 22, . . . , 2n. If the manufacturing device 21, 22, . . . , 2n is an exposure device, the device parameter includes exposure amount, synchronization precision between the stage mounted with the wafer and the reticle, humidity in the unit, following precision of focus control with respect to inclination of the wafer, bumps on the wafer surface or the like, rotation correction amount with respect to deflected distortion of the exposure beam and the like. If the manufacturing device 21, 22, . . . , 2n is a device including a chamber such as film forming device, diffusion device, and thin film depositing film device of vacuum processing system, the device parameter includes temperature at a plurality of areas in the chamber, susceptor temperature, temperature at a plurality of areas in the outer wall of the chamber, chamber pressure, gas flow rate, opening of a valve for controlling the gas flow rate and the like. If the manufacturing devices 21, 22, . . . , 2n are devices including electrodes such as dry etching device and ion injection device of plasma processing system, the device parameter includes radio frequency (RF) matching position, RF voltage (advancing wave voltage, reflected wave voltage), and the like in addition to various parameters of the vacuum processing system mentioned above. The device parameter may be acquired in unit of shot areas of the exposure device or in unit of chip areas of the wafer.

The device parameter acquiring units 31, 32, . . . , 3n acquire the device parameters of each of the manufacturing device 21, 22, . . . 2n, and, for example, transmit the information to a network system such as local area network (LAN) installed in the clean room.

The device parameter collecting server 40 collects the device parameters transmitted from the device parameter acquiring units 31, 32, . . . , 3n, and stores the device parameters in the device parameter database 41 as time series data as shown in FIG. 2.

The production management database 46 shown in FIG. 1 is connected to a production management server 45. The production management server 45 stores the processing history information such as product name, lot number, wafer number, chip number, shot number and the like processed by each manufacturing device 21, 22, . . . , 2n in the production management database 46 along with time information.

Figure 3:
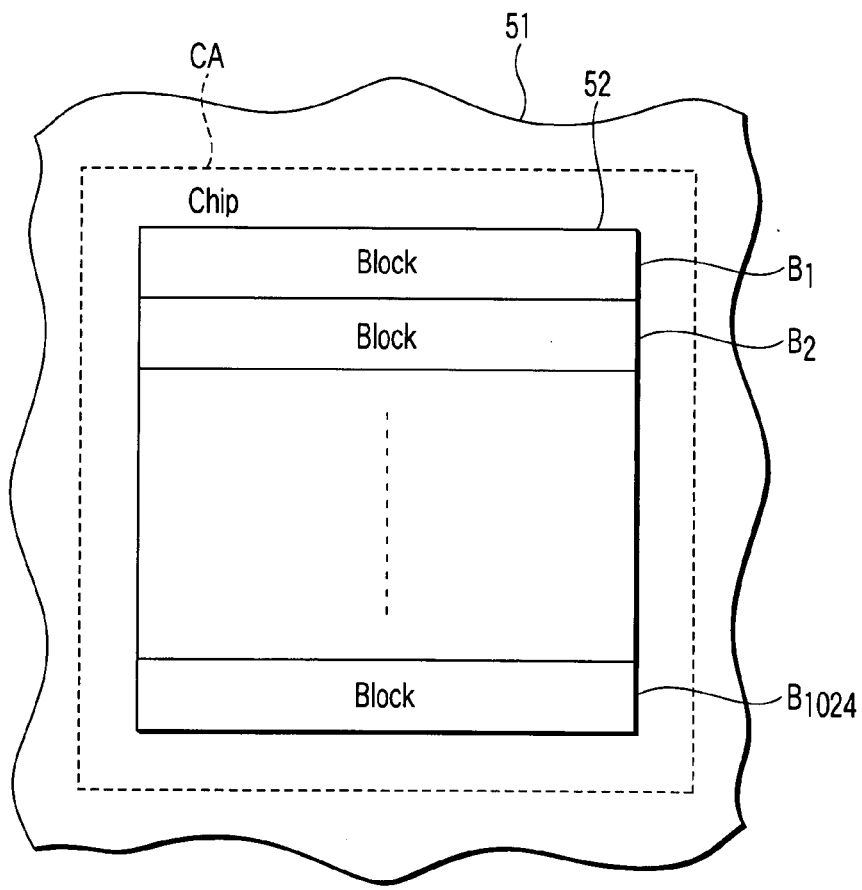
FIG. 3 is a schematic view showing one example of a memory cell array according to the embodiment of the present invention.

The wafer test database 44 is connected to a tester server 43. A tester 42 is connected to the tester server 43. The tester 42 performs a wafer test including various electrical tests on each of a plurality of circuit blocks formed on the wafer terminated with the wafer process in the clean room. In the present embodiment, an example in which the testing object is a memory product will be described. As shown in FIG. 3, a memory cell array 52 in the chip area CA arrayed on the wafer 51 includes 1024 blocks $B_1, B_2, \ldots, B_{1024}$ with a size smaller than the size of the chip area CA in the memory product. The tester 42 acquires the information on the defect distribution in units of blocks $B_1, B_2, \ldots, B_{1024}$ in the wafer 51 surface from the result of the wafer test as "sub-chip test data". The sub-chip test data is not limited to the information on the defect distribution in units of blocks $B_1, B_2, \ldots, B_{1024}$, and merely needs to be a wafer test result indicating the defect distribution in the area with a size smaller than the size of the chip area. The information on the defect distribution is acquired in an area in units of blocks $B_1, B_2, \ldots, B_{1024}$ herein since acquisition of the sub-chip test data indicating the information on the defect distribution in an area in units of bits smaller than the area in units of blocks $B_1, B_2, \ldots, B_{1024}$ of the memory cell array 52 takes much time in measurement and the amount of data thereof is enormous.

The tester server 43 shown in FIG. 1 stores the sub-chip test data acquired by the tester 42 in the wafer test database 44 along with the auxiliary information such as product name, lot number, wafer number, and chip number.

The data acquiring section 11 of the CPU 1 acquires the time series data of the device parameter read from the device parameter database 41 along with the processing history information such as product name, lot number, wafer number, chip number, and shot number read from the production management server 45. Furthermore, the data acquiring section 11 also acquires the sub-chip test data read from the wafer test database 44 along with the auxiliary information such as product name, lot number, wafer number, chip number, and shot number.

The pattern classifying section 12 of the CPU 1 assembles the defect distribution acquired from the sub-chip test data in units of shot areas SA of the wafer 51, which is the processing unit of the lithography step, and classifies the defect distribution into defect patterns in units of shot areas SA, as shown in FIG. 4. That is, one example specific to the detection of drawbacks in the lithography step will be explained in the present embodiment. The shot area SA equals the size of the chip area CA shown in FIG. 3. The size of the shot area SA may be larger than or smaller than the size of the chip area CA.

Figure 6:
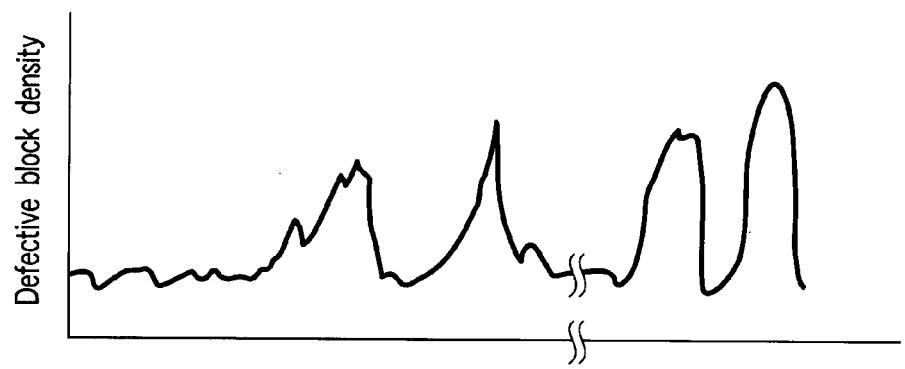
FIG. 6 is a graph showing one example of a feature quantity waveform of a defect distribution shown in FIG. 5.
Figure 7:
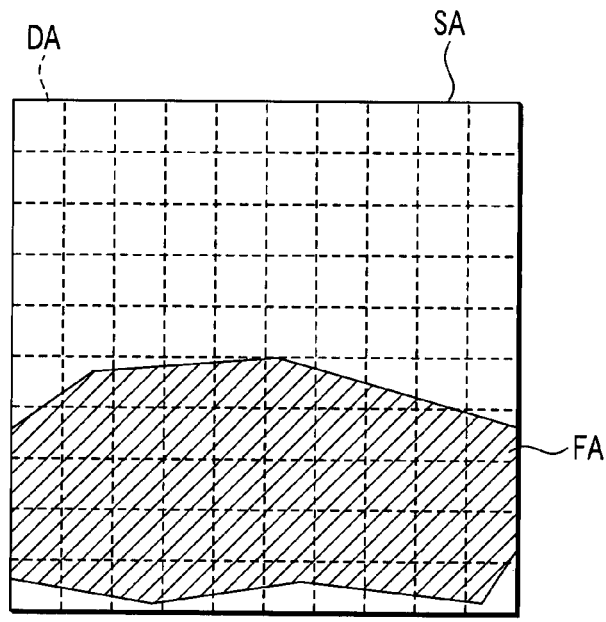
FIG. 7 is a schematic view showing another example of the defect distribution in a shot area according to the embodiment of the present invention.
Figure 8:
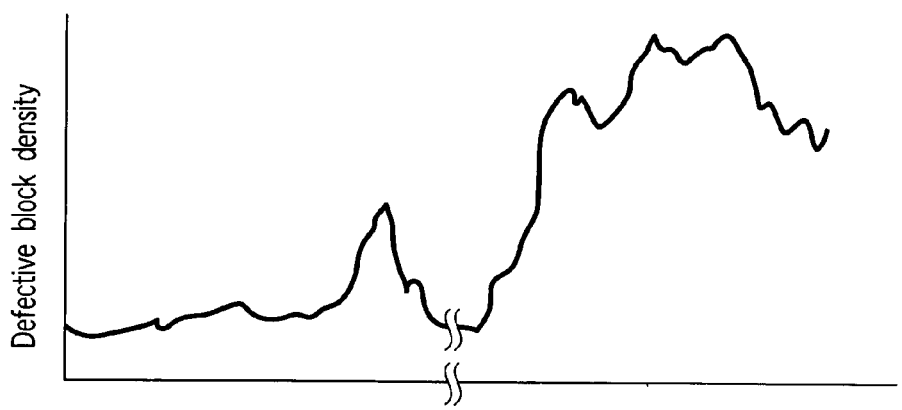
FIG. 8 is a graph showing one example of a feature quantity waveform of a defect distribution shown in FIG. 7.
Figure 9:
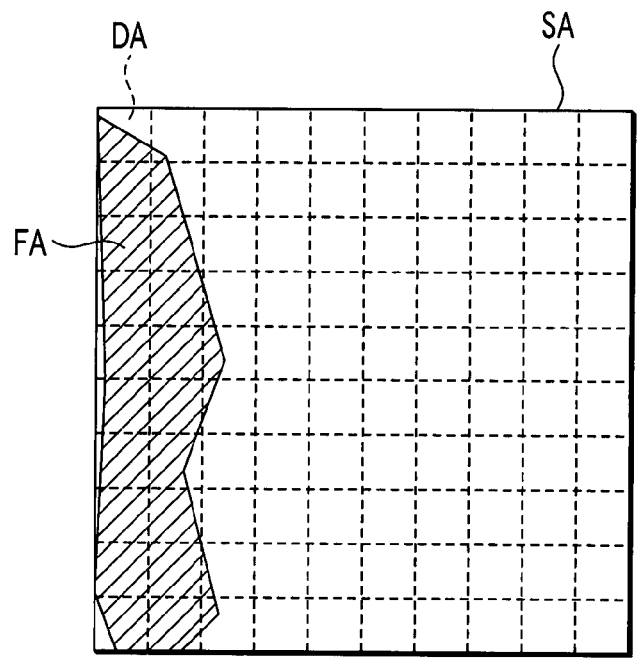
FIG. 9 is a schematic view showing another further example of the defect distribution in a shot area according to the embodiment of the present invention.
Figure 10:
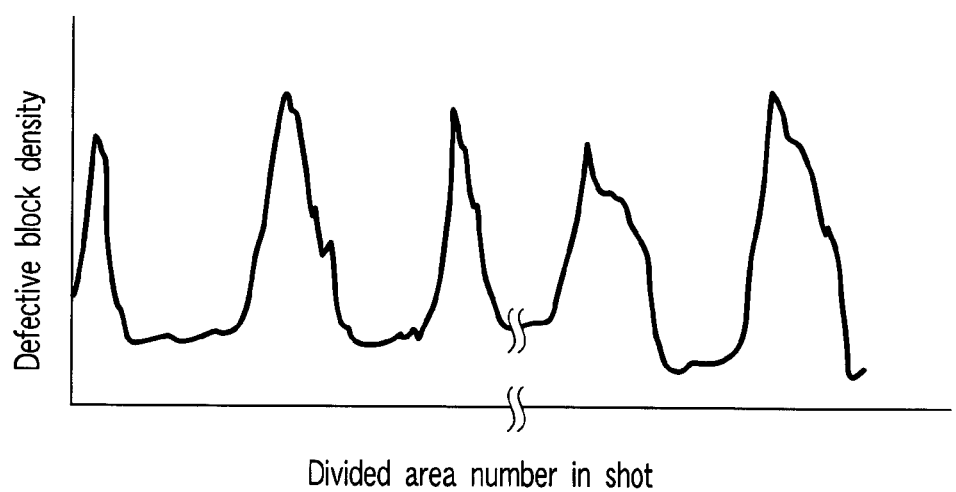
FIG. 10 is a graph showing one example of a feature quantity waveform of a defect distribution shown in FIG. 9.

FIG. 5 shows the defect distribution FA deflected to the lower right side in the shot area SA with diagonal lines. The defect distribution FA is an area (clustering defect area) in which the density of the defective block is high. In defect pattern classification, the shot area SA is divided into, for example, 10 by 10 areas DA, as shown in FIG. 5. The size and number of the divided areas DA are not particularly limited. Each divided area DA includes, for example, about 1000 blocks of the memory cell array. The change (i.e., "change in feature quantity") in defect distribution FA, that is, defective block density in the shot area SA shown in FIG. 5 is indicated as a waveform (i.e., "waveform showing change in feature quantity") as shown in FIG. 6 by lining the divided areas DA in the shot area SA shown in FIG. 5 in the order from the left end to the right end and in the order from the upper most row to the lower most row in the horizontal axis. The "waveform indicating change in feature quantity" is hereinafter referred to as "feature quantity waveform". Furthermore, indication as "waveform indicating change in feature quantity" is hereinafter referred to as "feature quantity waveforming". The defect distribution FA deflected to the lower side in the shot area SA as shown in FIG. 7 is indicated as the feature quantity waveform as shown in FIG. 8. The defect distribution FA deflected to the left side in the shot area SA as shown in FIG. 9 is indicated as the feature quantity waveform as shown in FIG. 10. As shown in FIGS. 6, 8, and 10, the feature quantity waveform respectively has a unique shape due to the deflection mode of the defect distribution FA.

Figure 11:
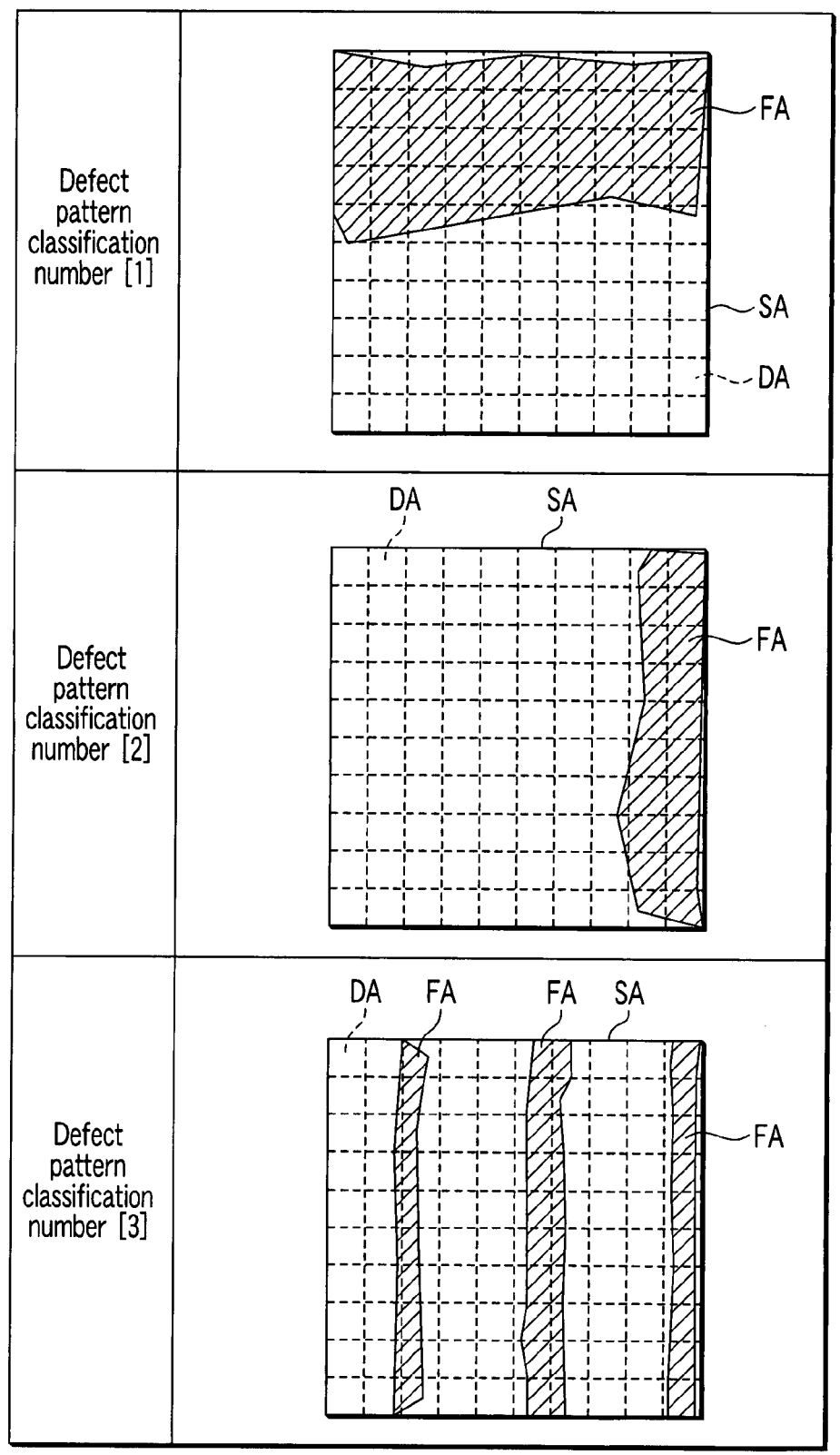
FIG. 11 is a table showing one example of a classification result of the defect pattern in the shot area according to the embodiment of the present invention.

Moreover, the pattern classifying section 12 of the CPU 1 classifies the defect distribution FA of a plurality of shot areas SA to a plurality of defect patterns based on the feature quantity waveform as shown in FIGS. 6, 8, and 10. In classification of the defect pattern, for example, the correlation function of the feature quantity waveform of the defect distribution FA in each shot area SA is calculated, the calculated correlation function is compared with a threshold value to determine the similarity between the plurality of defect distributions FA, and the defect distributions FA with similarity are grouped. As a result of classification of the defect pattern, the defect distribution acquired by the sub-chip test data, for example, for 100 lots serving as the classifying target is classified into three types of defect patterns of, for example, defect pattern classification numbers [1] to [3], as shown in FIG. 11. In FIG. 11, the defect pattern of defect pattern classification number [1] is a pattern in which the defect distribution FA is deflected to the upper side in the shot area SA. The defect pattern of defect pattern classification number [2] is a pattern in which the defect distribution FA is deflected to the right end in the shot area SA. The defect pattern of defect pattern classification number [3] is a pattern in which the defect distribution FA is deflected to a longitudinal strip form in the shot area SA. The classification result of the defect pattern is stored in the defect pattern classifying database 6 along with the auxiliary information such as product name, lot number, wafer number, chip number, and shot number in which each defect pattern is found.

The feature quantity calculating section 13 of the CPU 1 feature quantifies the waveform of the time series data of the device parameter as shown in FIG. 2. Here, "feature quantification" refers to expressing the waveform of the time series data of a constant period of the device parameter with one scalar quantity (feature quantity). In the present embodiment, the time series data of the device parameter in the processing period of the shot area SA is feature quantified in units of shot areas SA. The "feature quantified time series data of device parameter" is hereinafter referred to as "device parameter waveform feature quantity". The method of feature quantification uses, for example, the maximum value, mean value, or variance of the waveform of the time series data in the processing period, but other statistical values may be used. Each device parameter waveform feature quantity is stored in the feature quantity database 7 along with the auxiliary information such as product name, lot number, wafer number, chip number, and shot number.

The significant difference test section 14 of the CPU 1 associates the device parameter waveform feature quantity of the device parameter waveform feature quantity number [i] (i: positive integer) read from the feature quantity database 7 and the defect pattern of the defect pattern classification number [j] (j: positive integer) read from the defect pattern classifying database 6, as shown in FIG. 12, using the product name, lot number, wafer number, chip number, and shot number as common terms.

Furthermore, the significant different test section 14 defines the shot area in which the defect pattern of defect pattern classification number [j] is present as "abnormal shot", and the shot area in which the defect pattern of defect pattern classification number [j] is not present as the "normal shot". The significant different test section 14 calculates the frequency distribution with defect pattern and the frequency distribution without the defect pattern of the defect pattern classification number [j] with respect to the device parameter waveform feature quantity of the device parameter waveform feature quantity number [i]. That is, the significant difference test section 14 calculates the frequency distribution of the abnormal shot and the frequency distribution of the normal shot of the defect pattern classification number [j] for the device parameter waveform feature quantity of the device parameter waveform feature quantity number [i]. Furthermore, the significant difference test section 14 performs the significant difference test between the frequency distribution of the abnormal shot and the frequency distribution of the normal shot of the device parameter waveform feature quantity with respect to all combinations of the device parameter waveform feature quantity number [i] and the defect pattern classification number [j], and calculates the significant difference test value Pij. For example, $\chi^2$ test is performed as the significant difference test. Moreover, the significant difference test section 14 determines that there is significant difference when the significant difference test value Pij is less than or equal to a test reference value (e.g., 0.05).

For example, the frequency distribution of the abnormal shot and the frequency distribution of the normal shot of the defect pattern classification number [1] with respect to the device parameter waveform feature quantity of the device parameter waveform feature quantity number [1] is calculated by the significant difference test section 14, as shown in FIG. 13. The frequency distribution of the abnormal shot and the frequency distribution of the normal shot shown in FIG. 13 are similar to each other. The significant difference test value P11 between the frequency distribution of the abnormal shot and the frequency distribution of the normal shot is larger than or equal to the test reference value, and thus is determined that there is no significant difference in the significant difference test.

Furthermore, the frequency distribution of the abnormal shot and the frequency distribution of the normal shot of the defect pattern classification number [2] with respect to the device parameter waveform feature quantity of the device parameter waveform feature quantity number [2] is calculated by the significant difference test section 14, as shown in FIG. 14. The frequency distribution of the abnormal shot and the frequency distribution of the normal shot shown in FIG. 14 are different from each other. The significant difference test value P12 between the frequency distribution of the abnormal shot and the frequency distribution of the normal shot is less than or equal to the test reference value, and thus is determined that there is significant difference in the significant difference test.

The defect detecting section 15 of the CPU 1 detects the device parameter corresponding to the device parameter waveform feature quantity number [i] determined that the significant difference test value has significant difference as the cause of defect of the defect pattern of the defect pattern classification umber [j]. As shown in FIG. 15, the device parameters of the device parameter waveform feature quantity numbers [1] to [6], for example, includes the exposure amount, synchronization precision, humidity in the unit, focus following precision, beam rotation correction amount, developing solution temperature, which are parameters related to the lithography step. For example, the exposure amount is detected as the cause of defect with respect to the defect pattern of the defect pattern classification number [1]. Furthermore, for example, the humidity in the unit is detected as the cause of defect with respect to the defect pattern of the defect pattern classification number [2]. Furthermore, for example, the synchronization precision is detected as the cause of defect with respect to the defect pattern of the defect pattern classification number [3].

The defect detecting section 15 further stores the state of abnormality occurrence of the device parameter detected as the cause of defect and the abnormality occurrence information such as the process name, manufacturing device name, device parameter name, and feature quantity algorithm used in calculating the feature quantity relevant to the abnormality occurrence in the real time monitor database 8, as shown in FIG. 16.

An input device 2, an output device 3, and a main storage device 4 are connected to the CPU 1 shown in FIG. 1. The input device 2 refers to equipments such as keyboard and mouse. When input operation is performed through the input device 2, the information corresponding to the input operation is transmitted to the CPU 1. The output device 3 refers to screens such as monitor, and liquid crystal display (LCD), light emitting diode (LED) panel, electroluminescent (EL) panel, or the like may be used. The output device 3 is controlled by the CPU 1, and displays the sub-chip test data obtained from the electrical test, calculation result of the feature quantity of quantifying the device parameter, and the like. The main storage device 4 temporarily stores the data in the middle of calculation or in the middle of analysis in the computation by the CPU 1. The program storage device 5 stores the program for the CPU 1 to execute classification of the defect pattern, feature quantification of the device parameter, statistical computation of feature quantity analysis, or the like.

A defect detection method according to the present embodiment of the present invention will now be described using the flowchart shown in FIG. 17.

First, assumption is made that the plurality of manufacturing devices 21, 22, . . . , 2n are processing the wafers in units of lots to manufacture a specific semiconductor device. The state of the plurality of manufacturing devices 21, 22, . . . , 2n for sequentially processing the plurality of lots is shown. The time series data of the device parameter as shown in FIG. 2 is acquired in the device parameter acquiring units 31, 32, . . . , 3n in correspondence to the course of the step, respectively. The time series data of the device parameter acquired by each device parameter acquiring units 31, 32, . . . , 3n is stored in the device parameter database 41 by the device parameter collecting server 40. The processing history information such as product name, lot number, wafer number, chip number and shot number processed in each of the manufacturing device 21, 22, . . . , 2n is stored in the production management database 46 along with the time information by the production management server 45. In addition, the wafer test including various electrical tests is performed by the tester 42 on each of the plurality of circuit block formed on the wafer of the semiconductor device terminated with the wafer process. The sub-chip test data or the information on the defect distribution in the area (area in units of blocks) with a size smaller than the size of the chip area is created in the tester server 43 that manages the tester 42 as shown in FIG. 4, and stored in the wafer test database 44 along with the auxiliary information such as product name, lot number, wafer number, chip number, and shot number.

(a) In step S1, the data acquiring section 11 of the CPU 1 shown in FIG. 1 acquires the time series data of the plurality of device parameters indicating the state of each of the plurality of manufacturing device 21, 22, . . . , 2n from the device parameter database 41. In step S2, the data acquiring section 11 acquires the time series data of the product name, lot number, wafer number, chip number, and shot number processed in each of the plurality of manufacturing devices 21, 22, . . . , 2n from the production management database 46. In step S3, the data acquiring section 11 acquires the sub-chip test data, which is the result of the wafer test result for the area with a size smaller than the size of the chip area, from the tester database 43 along with the auxiliary information such as product name, lot number, wafer number, chip number, and shot number.

(b) In step S4, the pattern classifying section 12 assembles the defect distribution FA obtained from the sub-chip test data in units of shot areas SA, as shown in FIG. 4, and feature quantity waveforms the assembled defect distribution FA in units of shot areas SA. In step S5, the feature quantity waveforming of step S4 is repeated until the pattern of the feature quantity of all target shot areas SA is feature quantity waveformed.

(c) In step S6, the pattern classifying section 12 classifies the defect distribution FA in the shot area SA to the defect pattern as shown in FIG. 11 using the feature quantity waveform in which the defect distribution FA is grouped for every shot area SA. The classification result of the defect pattern is stored in the defect pattern classification database 6 with the auxiliary information such as product name, lot number, wafer number, chip number and shot number.

(d) In step S7, the feature quantity calculating section 13 calculates the device parameter waveform feature quantity obtained by statistically processing and quantifying each time series data of the plurality of device parameters in units of shot areas. The device parameter waveform feature quantity is stored in the feature quantity database 7 with the auxiliary information such as product name, lot number, wafer number, chip number, and shot number.

(e) In step S8, the significant difference test section 14 associates the device parameter waveform feature quantity number [i] and the defect pattern classification number [j] using the product name, lot number, wafer number, chip number, and shot number as the common term, as shown in FIG. 12. Since the significant difference test value Pij of all the combinations of the device parameter waveform feature quantity number [i] and the defect pattern of the defect pattern classification number [j] must be calculated, the device parameter waveform feature quantity number [i] is first assumed as 1 and the defect pattern classification number [j] as 1.

(f) In step S9, the significant difference test section 14 defines the shot area in which the defect pattern of the defect pattern classification number [j] is present as the "abnormal shot", and the shot area in which the defect pattern of the defect pattern classification number [j] is not present as the "normal shot". The significant difference test section 14 calculates the frequency distribution with defect pattern and the frequency distribution without the defect pattern of defect pattern classification number [j] with respect to the device parameter waveform feature quantity of the device parameter waveform feature quantity number [i] as shown in FIGS. 13 and 14. That is, the significant difference test section 14 calculates the frequency distribution of the abnormal shot and the frequency distribution of the normal shot of the defect pattern classification number [j] for the device parameter waveform feature quantity of the device parameter waveform feature quantity number [i]. Furthermore, the significant difference test section 14 performs the significant difference test between the frequency distribution of the abnormal shot and the frequency distribution of the normal shot for every defect pattern, and calculates the significant difference test value Pij.

(g) In step S10, the calculation of the significant difference test value Pij of step S9 is repeated until the significant difference test value Pij for all the combinations of the device parameter waveform feature quantity number [i] and the defect pattern classification number [j] is calculated.

(h) In step S11, the defect detecting section 15 compares each significant difference test value Pij and the test reference value, and detects the device parameter corresponding to the device parameter waveform feature quantity number [i] with significant difference as the cause of defect of the defect pattern of the corresponding defect pattern classification umber [j], as shown in FIG. 15. The defect detecting section 15, as shown in FIG. 16, further stores the state of abnormality occurrence of the device parameter detected as the cause of defect of the defect pattern and the abnormality occurrence information such as the process name, manufacturing device name, device parameter name, and feature quantity algorithm corresponding to the abnormal occurrence used in detecting the abnormality in the real time monitor database 8. In the manufacturing devices 21, 22, . . . , 2n, the production efficiency of the semiconductor device is enhanced by correcting the area of the manufacturing devices 21, 22, . . . , 2n corresponding to the device parameter detected as the cause of defect based on the abnormality occurrence information.

According to the defect detection system and the defect detection method according to the embodiment of the present invention, the pattern classification of the sub-chip test data, which is the information on the defect distribution in the area with a size smaller than the size of the chip area and the device parameter are associated to detect, at high precision, the cause of defect that was not found in the defect pattern classification/defect detection using the tendency in the wafer surface in the area with a size larger than the size of the chip area, as described above.

Figure 17:
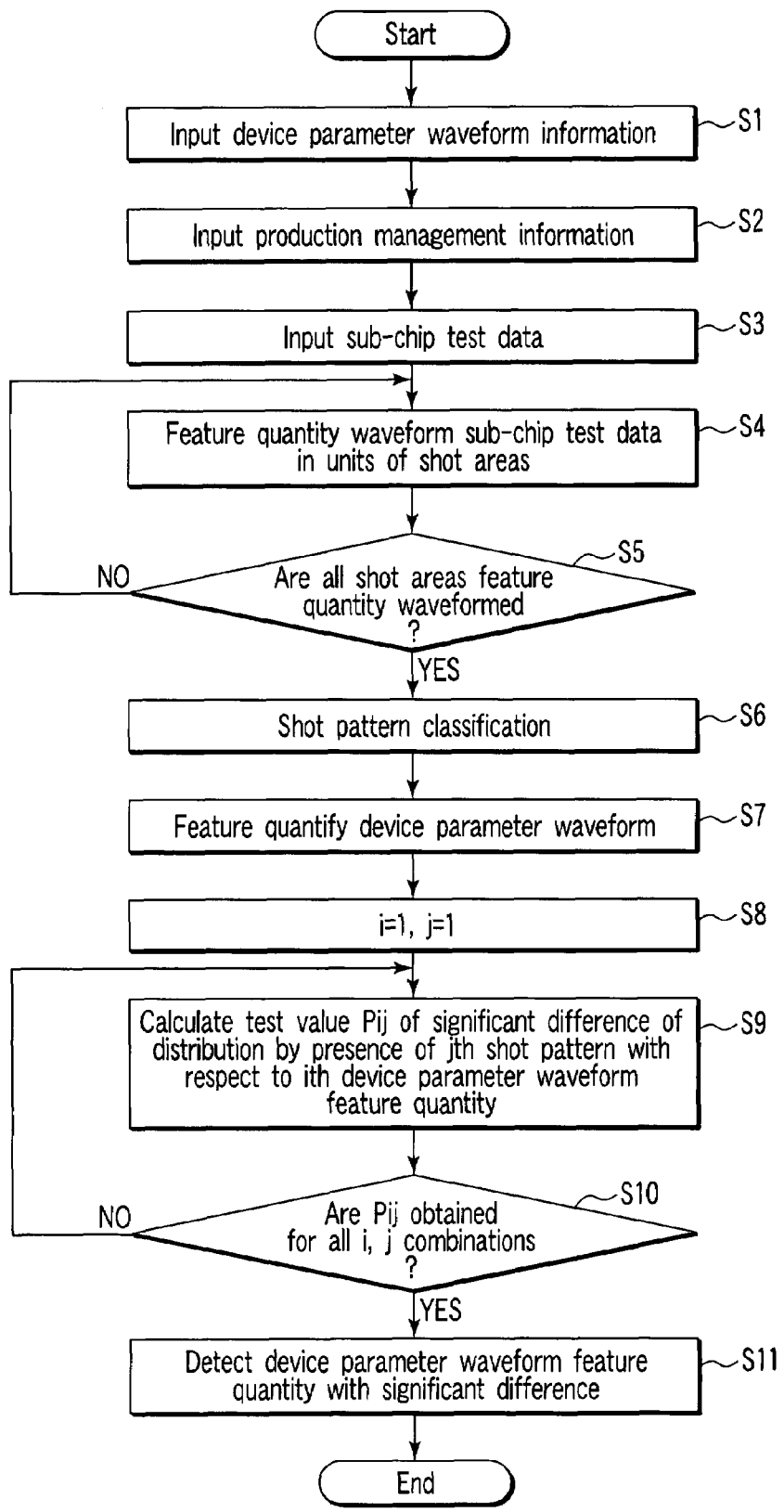
FIG. 17 is a flowchart showing one example of a defect detection method according to the embodiment of the present invention.

A series of procedures shown in FIG. 17, that is, a command to acquire the time series data of the plurality of device parameter respectively indicating the state of the plurality of manufacturing devices, a command to acquire the information on the defect distribution in the area with a size smaller than the size of the chip area of the wafer processed in each of the plurality of manufacturing devices, a command to assemble the information on the defect distribution in units of shot areas of the exposure device and classify the assembled defect distribution to defect patterns, a command to statistically process the time series data and calculate the feature quantity, a command to calculate the occurrence frequency distribution of the shot area in which the defect pattern with respect to the feature exists and the occurrence frequency distribution of the shot area in which the defect pattern with respect to the feature quantity does not exist, a command to test the presence or absence of significant difference between the frequency distributions in units of shot areas, and a command to detect the device parameter corresponding to the feature quantity determined to have significant difference as a result of the significant difference test as the cause of defect of the defect pattern can be executed by controlling the defect detection system shown in FIG. 1 by the program of the algorithm equivalent to that of FIG. 17. This program is, for example, stored in the program storage device 5. Furthermore, this program may be stored on a computer readable recording medium, and the series of procedures of the embodiment of the present invention may be executed by reading this recording medium by the program storage device 5 of the defect detection system. "Computer readable recording medium" herein refers to, for example, the medium capable of recording programs such as external memory device of the computer, semiconductor memory, magnetic disc, optical disc, magnetic optical disc, and magnetic tape. Specifically, "computer readable recording medium" includes flexible disc, CD-ROM, MO disc, and the like.

Figure 18:
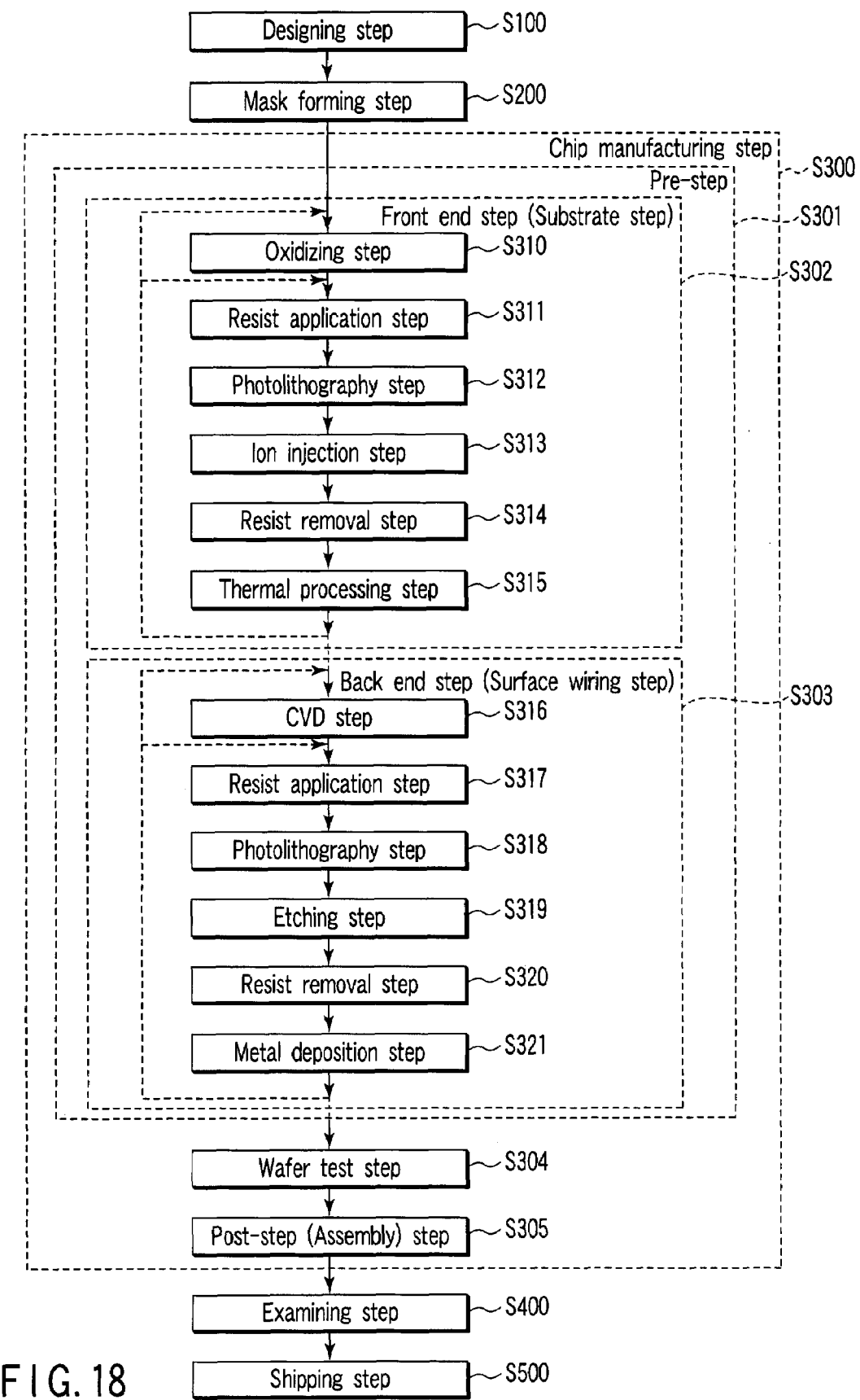
FIG. 18 is a flowchart for explaining one example of a method of manufacturing a semiconductor device according to the embodiment of the present invention.

The method of manufacturing the semiconductor device according to the embodiment of the present invention will now be described with reference to the flowchart of FIG. 18.

(a) In step S100, process simulation, lithography simulation, device simulation, and circuit simulation are performed, and the layout data (CAD data) is generated.

(b) In step S200, the mask data corresponding to the design pattern of the CAD data generated in step S100 is generated. The mask pattern is formed on the mask substrate based on the mask data, and photomask is formed. The photomask is formed for the number of sheets corresponding to each stage of the manufacturing step of the LSI, and a set of photomask is prepared.

(c) In the chip manufacturing step of step S300, the pre-step of step S301 and the post-step of step S305 are performed. The front end step (substrate step) of step S302 and the back end step (surface wiring step) of step S303 are performed in the pre-step of step S301. In the front end step in step S302, for example, oxidizing step in step S310, resist application step in step S311, photolithography step in step S312, selective ion injection step using the mask created in step S312 in step S313, resist removal step in step S314, thermal processing step in step S315 etc. are performed. FIG. 18 is a simplified frame format flowchart, and chemical vapor deposition (CVD) step may be performed in place of the oxidizing step in step S310. If selective etching using the mask formed in step S312 is performed in place of steps S313 to S315, various steps may be included such as removing the resist after such selective etching, performing ion injection, further performing etching after the removal of the resist, and the like. Various wafer processing steps such as selective ion injection and selective etching are repeated and performed in step S303. The process proceeds to step 303 after the series of steps is terminated.

(d) The back end step in which the wiring process is performed on the substrate surface is performed in step S303. In the back end step, various wafer processing steps such as, for example, CVD step in step S316, resist application step in step S317, photolithography step in step S318, selective etching step using the mask formed in step S318 in step S319, resist removal step in step S320, metal deposition step to the via hole and damascene groove formed in step S319 in step S321, and the like are repeated and performed. The back end step is not limited to FIG. 18, for example, and metal deposition step in step S321 may be performed after the CVD step of step S316, and the etching step of steps S317 to 320 may be performed thereafter. The process proceeds to step S304 after the multi-layer wiring configuration is completed by the series of steps.

(e) The wafer test by the tester 42 is performed in the wafer test step in step S304. The defect detection system shown in FIG. 1 detects the cause of defect of the semiconductor device as described in the procedures of steps S1 to S11 shown in FIG. 17. That is, the data acquiring section 11 acquires the time series data of the device parameter of each of the plurality of manufacturing devices including the exposure device, and the information on the defect distribution in the area with a size smaller than the size of each of the plurality of chip areas arrayed on the wafer to be processed by each of the plurality manufacturing devices. The pattern classifying section 12 then assembles the information on the defect distribution in units of shot areas of the exposure device or in units of chip areas, and classifies the assembled defect distribution to defect patterns. The feature quantity calculating section 13 statistically processes the time series data and calculates the feature quantity. The significant difference test section 14 calculates the occurrence frequency distribution of the shot area or the chip area in which the defect pattern with respect to the feature quantity exists and the occurrence frequency distribution of the shot area or the chip area in which the defect pattern with respect to the feature quantity does not exist, and determines the presence or absence of significant difference between the calculated frequency distributions. If determined that significant difference is present, the defect detecting section 15 detects the device parameter corresponding to the feature quantity as the cause of defect of the defect pattern.

(f) In the post-step in step S305, a package assembly step of dividing the wafer into chips of a predetermined size, mounting each divided chip on the packaging substrate, connecting the electrode pads on the chip and the leads of the lead frame, and the like. After being subjected to examination in step S400, the semiconductor device is shipped in step S500.

According to the manufacturing method of the semiconductor device according to the embodiment of the present invention, the cause of defect can be detected at high precision in units of shot areas of the exposure device in steps S312 and S318 in the wafer test step in step S304 by the defect detection using the procedures of steps S1 to S11 shown in FIG. 17. The device parameter of the exposure device detected as the cause of defect is monitored and the area related to the device parameter are improved, so that reliability of the semiconductor device is enhanced and high yield can be achieved.

(First Variant)

Figure 19:
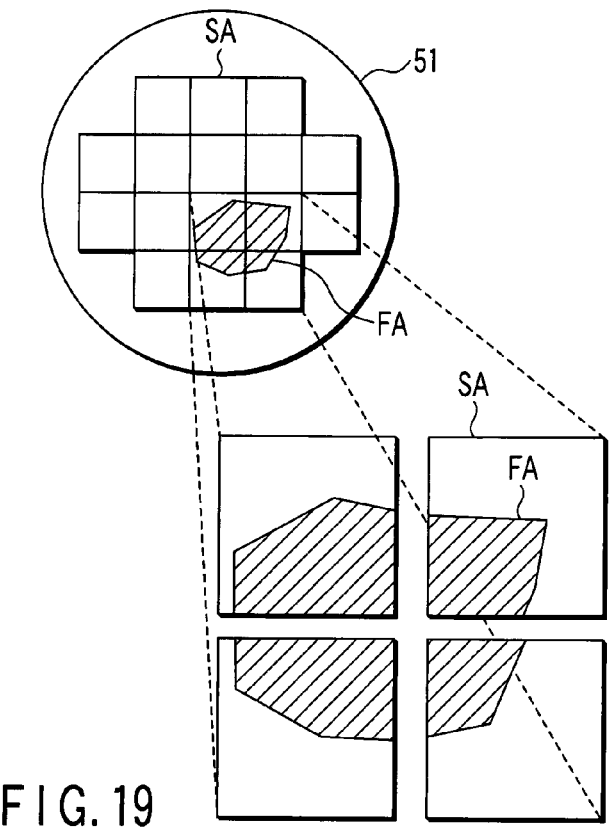
FIG. 19 is a schematic view for explaining the defect pattern without periodicity between the shot areas according to a first variant of the embodiment of the present invention.

A case in which the defect distribution FA is present not independently in one shot area SA but over a plurality of adjacent shot areas SA will be explained as a first variant of the embodiment of the present invention. As shown in FIG. 19, the defect distribution FA exists over four adjacent shot areas SA. The device parameter that becomes the cause of defect of the defect distribution FA cannot be detected even if the defect distribution FA is classified into units of shot areas SA. The classification of the defect pattern is performed after excluding the defect distribution FA without periodicity between the shot areas SA.

Figure 20:
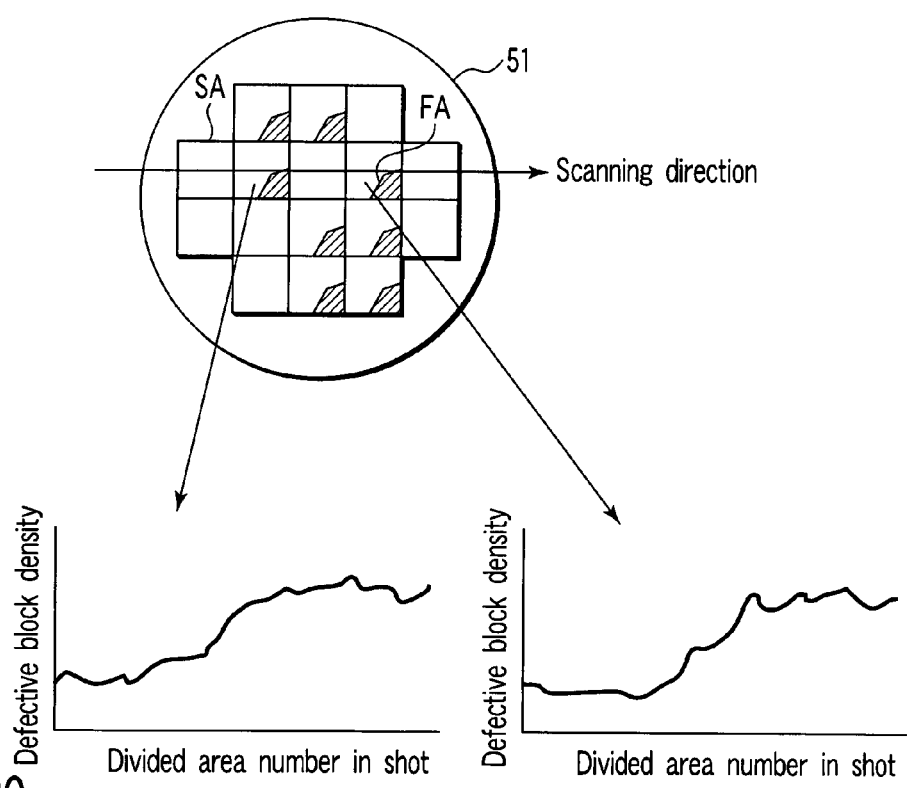
FIG. 20 is a schematic view for explaining defect pattern classification according to the first variant of the embodiment of the present invention.

For example, the pattern classifying section 12 extracts the plurality of shot areas SA of one certain row in the sub-chip test data as shown in FIG. 20, one-dimensionally profiles the defect distribution FA in each of the plurality of shot area SA, and determines the similarity between the one dimensional profile of the defect distribution FA of one shot area SA in the relevant row and the one dimensional profile of the defect distribution FA of another shot area SA in the relevant row. In determining the similarity, for example, the correlation function of the one dimensional profile of the defect distribution FA between the two shot areas is calculated, and the correlation function and the threshold value are compared to determine the similarity of the one dimensional profile between the two shot areas SA. If the one dimensional profile of the defect distribution FA of one shot area SA is similar to the one dimensional profile of one or more other shot areas SA belonging to the same row, determination is made as the defect distribution FA with periodicity in units of shot areas SA, and the defect distribution FA is classified into the defect pattern. On the other hand, if the one dimensional profile of the defect distribution FA of one shot area SA is not similar to the one dimensional profile of one or more other shot areas SA belonging to the same row, determination is made that periodicity is not found between the shot areas SA in the relevant defect distribution FA, and such defect distribution FA is excluded only in the classification of the defect pattern. The pattern classifying section 12 further classifies only the defect distribution FA determined to have periodicity to the defect pattern. A plurality of shot areas SA for one column may be extracted instead of extracting the plurality of shot areas SA for one row.

Figure 21:
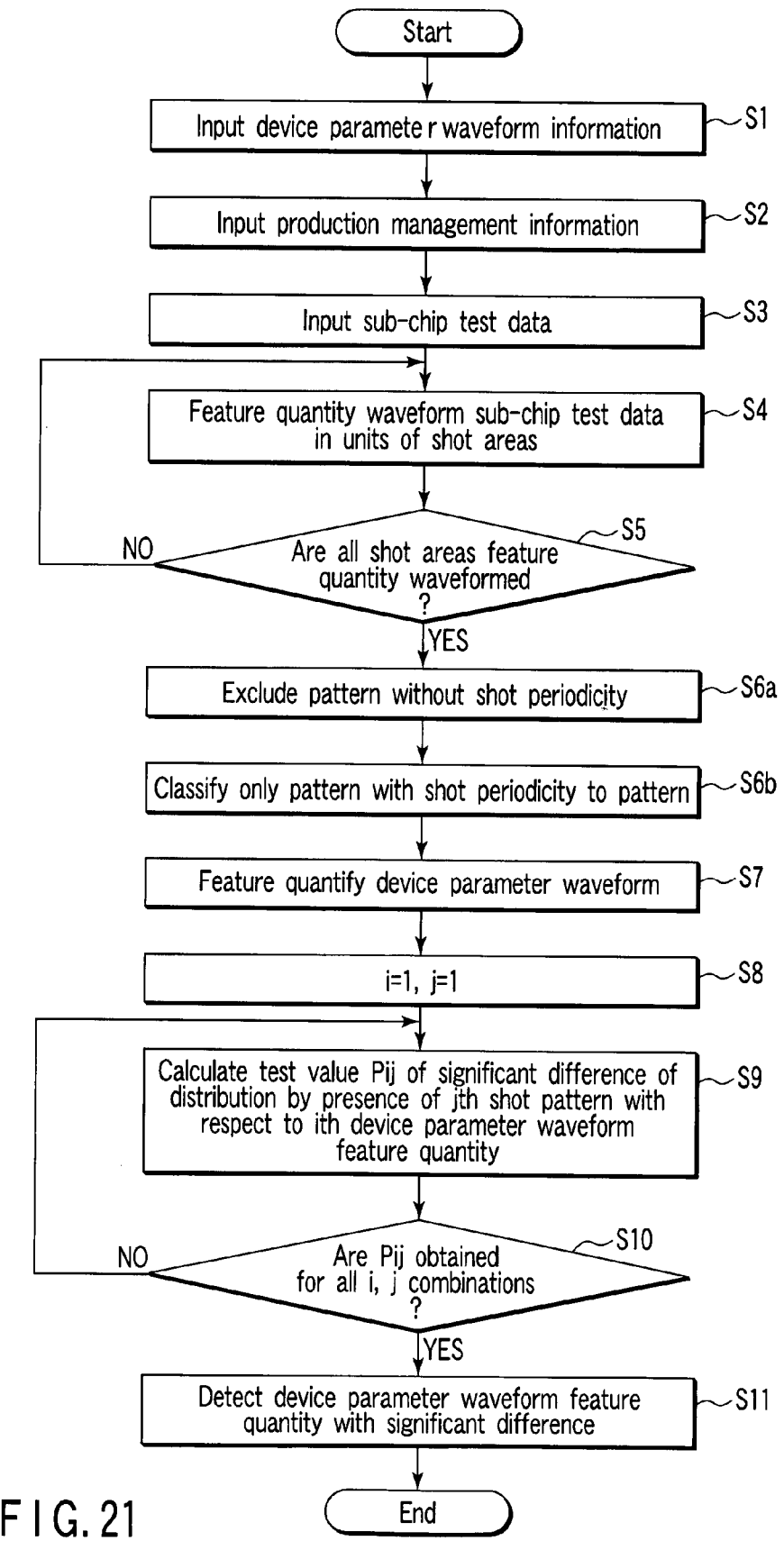
FIG. 21 is a flow chart for explaining one example of a defect detection method according to the first variant of the embodiment of the present invention.

In the defect detecting method according to the first variant of the embodiment of the present invention, the pattern classifying section 12 detects the defect distribution FA with periodicity between the shot areas SA, and excludes the defect distribution FA without periodicity in step S6a, as shown in FIG. 21. In step S6b, the pattern classifying section 12 classifies only the defect distribution FA determined to have periodicity to the defect pattern. Other procedures are substantially the same as the explanation of the procedures in steps S1 to S11 shown in FIG. 17, and thus redundant explanation will be omitted.

According to the first variant of the embodiment of the present invention, efficiency of defect detection is enhanced since classification to defect pattern is performed on the defect distribution FA with periodicity after excluding the defect distribution FA without periodicity in advance.

(Second Variant)

Figures 22, 23:
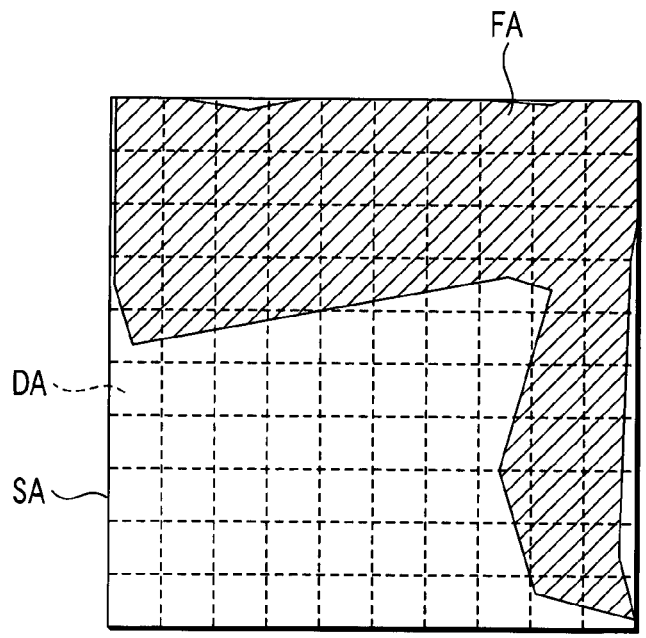
FIG. 22 is a schematic view showing a manufacturing flow according to a second variant of the embodiment of the present invention.
FIG. 23 is a schematic view showing a defect distribution of the shot area according to the second variant of the embodiment of the present invention.

A case of detecting the plurality of manufacturing devices (device parameter) with respect to one defect pattern as the cause of defect will be explained as a second variant of the embodiment of the present invention. Assumption is made that first to fourth machines of the manufacturing devices are present in the manufacturing steps A to D, respectively, as shown in FIG. 22. The cause of defect of each defect pattern of the defect pattern classification numbers [1] to [3] shown in FIG. 11 is assumed to be at the manufacturing parameters of third machine of manufacturing step A, the first machine of manufacturing step B, and the second machine of manufacturing step D.

Regarding a wafer processed by the third machine in manufacturing step A and the first machine in manufacturing step B is produced, if the device failure occurred when the wafer is processed in manufacturing step A and manufacturing step B, the defect distribution FA with a shape in which the defect pattern of the defect pattern classification number [1] and the defect pattern of the defect pattern classification number [2] are overlapped is generated, as shown in FIG. 23.

The pattern classifying section 12 classifies the defect distribution FA shown in FIG. 23 as the defect pattern of the defect pattern classification number [4]. The significant difference test section 14 performs a statistical test to determine that significant difference is present between the frequency distribution with defect and frequency distribution without defect of the defect pattern classification number [4] for each of the device parameter waveform feature quantity of the third machine of manufacturing step A and the device parameter waveform feature quantity of the first machine of manufacturing step B. The device parameter of the third machine of manufacturing step A and the device parameter of the first machine of manufacturing step B in which significant difference is present are detected as the cause of defect of the defect pattern classification number [4].

According to the second variant of the embodiment of the present invention, the plurality of manufacturing devices (manufacturing parameter) are detected as the cause of defect with respect to one defect pattern even if the cause of defect is found in the plurality of manufacturing devices (manufacturing parameter).

(Third Variant)

The maximum value, mean value, or variance is used as a method of feature quantification in the embodiment of the present invention, but various feature quantification algorithms used for feature quantification will be explained as a third variant of the embodiment of the present invention. The abnormality that can be detected from each of the algorithm of feature quantification of the time series data of the device parameter depends on the feature quantification algorithm.

For example, in one example of feature quantification algorithm, auto-correlation function is used. The ordinality of the time series data of the device parameter from lot arrival to provision is feature quantified as auto-correlation function. The auto-correlation function of the time series data of the device parameter is a feature quantity effective to the detection of the device parameter that fluctuates from the steady state in time of abnormality occurrence of the manufacturing device.

In another example of feature quantification algorithm, the matching rate in increasing or decreasing tendency in the fluctuation of the time series data of the device parameter is calculated as the device parameter waveform feature quantity regarding the plurality of device parameters acquired from one manufacturing device. The matching rate in increasing or decreasing tendency of the time series data of the plurality of device parameters is a feature quantity effective in detection of when the device parameters fluctuate with the same tendency due to the abnormality of the manufacturing device.

In addition, in another example of the feature quantification algorithm, the primary fitting coefficient of the tilt of when the time series fluctuation of the time series data of the device parameter is approximated with a linear function is calculated as the device parameter waveform feature quantity. The primary fitting coefficient is a feature quantity effective in detecting a drifting abnormality of the manufacturing device.

Furthermore, in another example of the feature quantification algorithm, the numerical value associated with the correlation coefficient of the correlation function indicating the difference with the time series data of the device parameter in the target lot sequence and the lot sequence period immediately before is calculated as the device parameter waveform feature quantity. The feature quantity obtained from the correlation coefficient of the target lot sequence and the lot sequence period immediately before is effective in detecting the change in time series data of the device parameter due to accidental abnormality occurrence.

In another further example of the feature quantification algorithm, the numerical value associated with the correlation coefficient of the correlation function indicating the presence or absence of time series data of the similar device parameter in the target lot sequence and the past lot sequence is obtained as the device parameter waveform feature quantity. The feature quantity obtained from the maximum correlation coefficient of the target lot sequence and the past lot sequence is effective in detecting the time series data of the abnormal device parameter of when the time series data of the device parameter differ by recipe.

Embodiments and variants of the present invention have been explained, but the present invention is not limited to such embodiments and variants.

Figure 24:
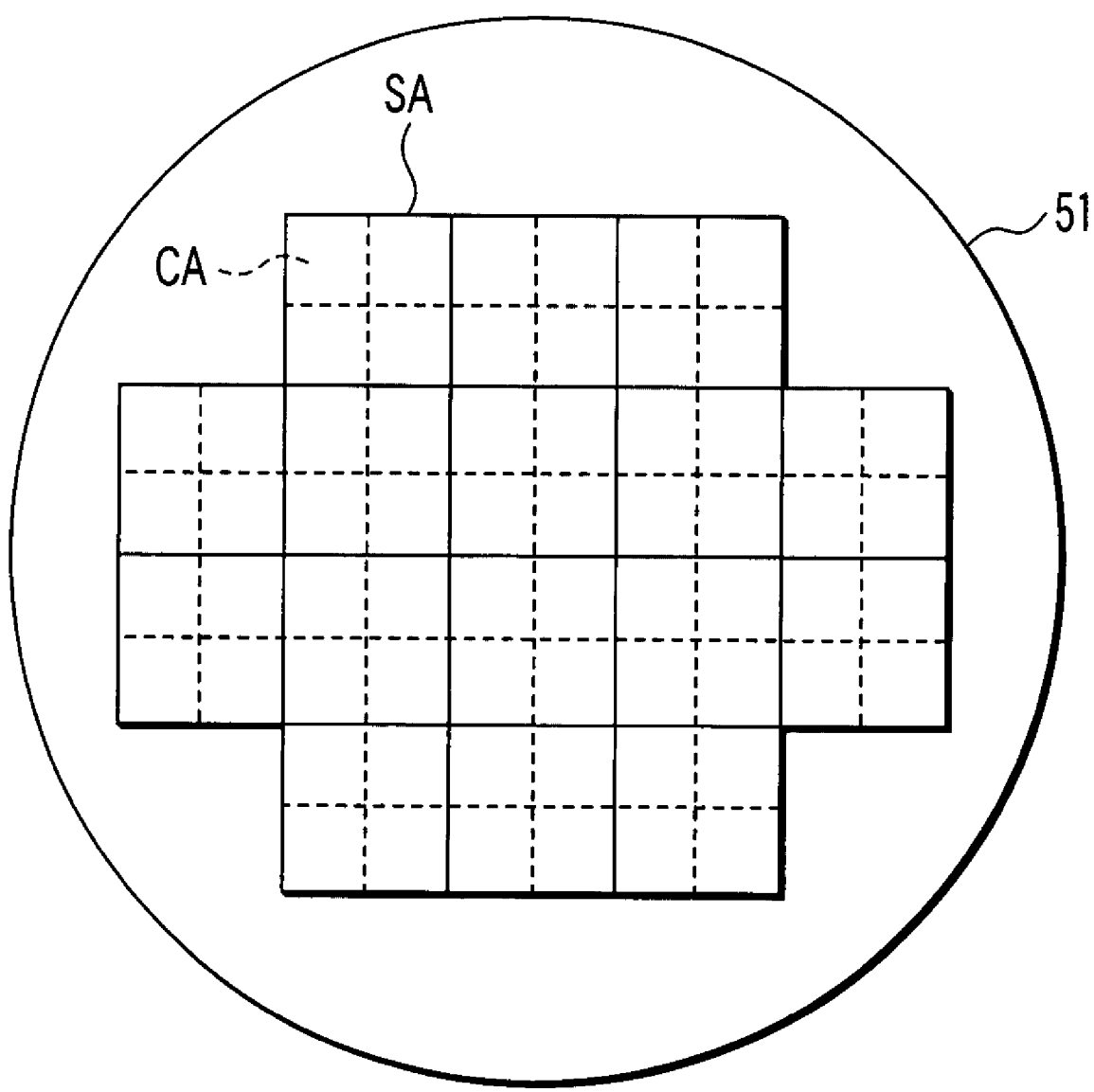
FIG. 24 is a schematic view showing one example of the sub-chip test data.

For example, the defect distribution FA obtained from the sub-chip test data is assembled in units of shot areas SA as shown in FIG. 4, and the assembled defect distribution FA is classified to the defect pattern in the embodiment of the present invention, but the defect distribution FA may be assembled in units of chip areas instead of in units of shot areas SA. For example, as shown in FIG. 24, the defect distribution obtained from the sub-chip test data is classified to the defect pattern in units of chip area CA, and the defect detection similar to the embodiment of the present invention is performed. For example, the device parameter of the chemical mechanical polishing (CMP) step is detected as the defect cause with respect to the defect pattern deflected to one end of the chip area CA.

In addition, a case of manufacturing the memory product as the semiconductor device has been explained in the embodiment of the present invention, but may be applied to manufacturing the logic product as the semiconductor device. In this case, the defective location of the circuit predicted from the test content with reference to the chip layout information instead of the defective block as the defect information of the sub-chip test data may be used.

Furthermore, the usage state of the redundancy (redundant circuit) such as memory product may be used instead of the defect block as the defect information of the sub-chip test data. In this case, the position in the chip area where redundancy is constantly used by a great amount may be detected by the classification algorithm similar to the defect pattern classification according to the embodiment of the present invention. This may be reflected on the circuit design to place larger amount of redundancy at the detected position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect detection system comprising:
   a data acquiring section that acquires time series data of a device parameter of each of a plurality of manufacturing devices including an exposure device, and information on defect distribution in an area with a size smaller than a size of each of a plurality of chip areas arranged on a wafer processed in each of the plurality of manufacturing devices;

a pattern classifying section that assembles the information on the defect distribution in units of shot areas of the exposure device or in units of chip areas, and classifies the assembled defect distributions to a defect pattern;

a feature quantity calculating section that statistically processes the time series data and calculates a feature quantity;

a significant difference test section that calculates an occurrence frequency distribution of the feature quantity in units of the shot area or the chip area in which the defect pattern exists and an occurrence frequency distribution of the feature quantity in units of the shot area or the chip area in which the defect pattern does not exist, and determines the presence or absence of a significant difference between the frequency distributions, the significant difference being determined to exist when a significant difference test value is smaller than a test reference value and determined not to exist when the significant difference test value is larger than the test reference value; and a defect detecting section that detects the device parameter corresponding to the feature quantity as the cause of defect of the defect pattern when the significant difference is determined to exist.

2. The defect detection system according to claim 1, wherein the pattern classifying section determines the presence or absence of periodicity of the defect distribution between the shot areas or between the chip areas, and classifies only the defect distribution determined to have periodicity to the defect pattern.

3. The defect detection system according to claim 1, wherein the pattern classifying section classifies a defect distribution with a shape in which the plurality of defect patterns are overlapped as an additional defect distribution; and the significant difference test section calculates an occurrence frequency distribution of the shot area or the chip area in which the additional defect pattern with respect to the feature quantity exists and an occurrence frequency distribution of the shot area or the chip area in which the additional defect pattern with respect to the feature quantity does not exist, and determines the presence or absence of significant difference between the frequency distributions.

4. The defect detection system according to claim 1, wherein the defect detecting section detects the plurality of device parameters as the cause of defect of the defect pattern.

5. The defect detection system according to claim 1, wherein the feature quantity calculating section calculates a waveform of the time series data of a constant period of the device parameter as one scalar quantity.

6. The defect detection system according to claim 1, wherein the significant difference detecting section determines as significantly different when a significant difference test value between the frequency distributions is less than or equal to a test reference value.

7. A defect detection method comprising the steps of:
acquiring by a data acquiring section a time series data of a device parameter of each of a plurality of manufacturing devices including an exposure device;
acquiring information on defect distribution in an area with a size smaller than a size of each of a plurality of chip areas arranged on a wafer processed in each of the plurality of manufacturing devices;

assembling the information on the defect distribution in units of shot areas of the exposure device or in units of chip areas, and classifying the assembled defect distributions to a defect pattern;

statistically processing the time series data and calculating a feature quantity; calculating an occurrence frequency distribution of the feature quantity in units of the shot area or the chip area in which the defect pattern exists and an occurrence frequency distribution of the feature quantity in units of the shot area or the chip area in which the defect pattern does not exist;

determining the presence or absence of a significant difference between the frequency distributions, the significant difference being determined to exist when a significant difference test value is smaller than a test reference value and determined not to exist when the significant difference test value is larger than the test reference value; and detecting the device parameter corresponding to the feature quantity as the cause of defect of the defect pattern when it the significant difference is determined to exist.

8. The defect detection method according to claim 7, wherein the classification of the defect distribution includes determining the presence or absence of periodicity of the defect distribution between the shot areas or between the chip areas, and classifying only the defect distribution determined to have periodicity to the defect pattern.

9. The defect detection method according to claim 7, wherein the classification of the defect distribution includes classifying a defect distribution with a shape in which the plurality of defect patterns are overlapped as an additional defect distribution; and the calculation of the occurrence frequency distribution includes that the significant difference test section calculates an occurrence frequency distribution of the shot area or the chip area in which the additional defect pattern with respect to the feature quantity exists and an occurrence frequency distribution of the shot area or the chip area in which the additional defect pattern with respect to the feature quantity does not exist, and the determination of the presence or absence of the significant difference includes determining the presence or absence of the significant difference between the frequency distributions.

10. The defect detection method according to claim 7, wherein the detection of the defect pattern includes detecting the plurality of device parameters as the cause of defect of the defect pattern.

11. The defect detection method according to claim 7, wherein the calculation of the feature quantity includes calculating a waveform of the time series data of a constant period of the device parameter as one scalar quantity.

12. The defect detection method according to claim 7, wherein the determination of the significant difference includes determining as significantly different when a significant difference test value between the frequency distributions is less than or equal to a test reference value.

13. The defect detection method according to claim 7, wherein the acquisition of the information on the defect distribution uses information of the use of a redundancy circuit of a memory.

14. A computer readable medium comprising a program executable by a computer to perform the steps of:
acquiring time series data of a device parameter of each of a plurality of manufacturing devices including an exposure device;

acquiring information on defect distribution in an area with a size smaller than a size of each of a plurality of chip areas arranged on a wafer processed in each of the manufacturing devices;

assembling the information on the defect distribution in units of shot areas of the exposure device or in units of chip areas, and classifying the assembled defect distributions to a defect pattern;

statistically processing the time series data and calculating a feature quantity; calculating an occurrence frequency distribution of the feature quantity in units of the shot area or the chip area in which the defect pattern exists and an occurrence frequency distribution of the feature quantity in units of the shot area or the chip area in which the defect pattern does not exist;

determining the presence or absence of a significant difference between the frequency distributions, the significant difference being determined to exist when a significant difference test value is smaller than a test reference value and determined not to exist when the significant difference test value is larger than the test reference value; and detecting the device parameter corresponding to the feature quantity as the cause of defect of the defect pattern when it the significant difference is determined to exist.

15. The program according to claim 14, wherein the command of classifying the defect distribution includes determining the presence or absence of periodicity of the defect distribution between the shot areas or between the chip areas, and classifying only the defect distribution determined to have periodicity to the defect pattern.

16. The program according to claim 14, wherein the command of classifying the defect distribution includes classifying a defect distribution with a shape in which the plurality of defect patterns are overlapped as an additional defect distribution; and the command of calculating the occurrence frequency distribution includes that the significant difference test section calculates an occurrence frequency distribution of the shot area or the chip area in which the additional defect pattern with respect to the feature quantity exists and an occurrence frequency distribution of the shot area or the chip area in which the additional defect pattern with respect to the feature quantity does not exist, and the command of determining the presence or absence of significant difference includes determining the presence or absence of the significant difference between the frequency distributions.

17. The program according to claim 14, wherein the command of detecting the defect pattern includes detecting the plurality device parameters as the cause of defect of the defect pattern.

18. The program according to claim 14, wherein the command of calculating the feature quantity includes calculating a waveform of the time series data of a constant period of the device parameter as one scalar quantity.

19. The program according to claim 14, wherein the command of determining the significant difference includes determining as significantly different when a significant difference test value between the frequency distributions is less than or equal to a test reference value.

* * * * *